(12) United States Patent
Hall-Goulle

(10) Patent No.: US 6,455,662 B2
(45) Date of Patent: Sep. 24, 2002

(54) CURABLE MIXTURES BASED ON EPOXY RESINS COMPRISING IMIDAZOLES

(75) Inventor: Véronique Hall-Goulle, Reinach (FR)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/728,991

(22) Filed: Dec. 4, 2000

Related U.S. Application Data

(62) Division of application No. 09/230,410, filed as application No. PCT/EP97/03811 on Jul. 16, 1997, now Pat. No. 6,174,985.

(30) Foreign Application Priority Data

Jul. 26, 1996 (CH) ............................................. 1875/96

(51) Int. Cl.$^7$ ........................... B32B 27/38; C08G 59/68
(52) U.S. Cl. ...................... 528/117; 428/413; 428/414; 525/523; 525/533
(58) Field of Search ............................... 428/413, 414; 525/523, 533; 528/117

(56) References Cited

U.S. PATENT DOCUMENTS

| | | | |
|---|---|---|---|
| 4,189,543 A | 2/1980 | Doorakian et al. | 521/128 |
| 5,623,023 A * | 4/1997 | Nishikubo | 525/327.3 |
| 6,174,985 B1 * | 1/2001 | Hall-Goulle | 528/117 |

FOREIGN PATENT DOCUMENTS

| | | |
|---|---|---|
| EP | 0124482 | 11/1984 |
| EP | 0193307 | 9/1986 |
| GB | 2067432 | 7/1981 |

OTHER PUBLICATIONS

Chem. Abstr. vol. 120, No. 14, (1994) 167301.
F. Trotta et al, Gazz. Chim. Ital., vol. 123, No. 10, (1993), pp. 559–562.
Chem. Abstr. vol. 97, No. 21, (1982), 182450.
Chem. Abstr. vol. 116, No. 19, (1992), 194215.
Chem. Abstr. vol. 117, No. 7, (1992), 69658.
Chem. Abstr. vol. 125, No. 20, (1996), 249390.
Database Beilstein XP 002045006, abstr. for Patchornik et al, J. Amer. Chem. Soc., vol. 79, (1957), pp. 6416–6420.
Database Beilstein XP 002045007, abstr. for Loozen et al, J. Org. Chem., vol. 40, (1975), p. 3279.
Database Beilstein XP 002045008, abstr. for Roechling et al, Z. Naturforsch. B. Anorg. Chem. Org. Chem . . . , vol. 25, (1970), pp. 1103–1110.
Database Beilstein XP 002045009, abstr. for Magn. Reson. Chem., vol. 26, (1988), p. 134.
Database Beilstein XP 002045010, abstr. for Helv. Chim. Acta, vol. 44, (1961), p. 2151.
Database Beilstein XP 002045011, abstr. for NL 6609596, GB 1154722.
Database Beilstein XP 002045012, abstr. for Tetrahedron Lett., vol. 23, No. 20, (1982), pp. 2113–2116.
Database Beilstein XP 002045013, abstr. for J. Chem. Res. Miniprint, (1991), pp. 1216–1239.
Database Beilstein XP 002045014, abstr. for Bull. Soc. Chim. Belg., vol. 101, No. 2, (1992), pp. 147–158.
Database Beilstein XP 002045015, abstr. for Bachi et al, J. Org. Chem., vol. 57, No. 17, (1992).
Database Beilstein XP 002045016, abstr. for Kamijo et al, Chem. Pharm. Bu. II., vol. 31, No. 11, (1983), pp. 4189–4192.
Database Beilstein XP 002045017, abstr. for Lee et al, Phosphorus, Sulfor Silicon Relat. Elem., vol. 45, (1989), pp. 35–46.
Bouillon et al, "Influence of Different Imidazole Catalysts on Epoxy–Anhydride Copolymerization and on Their Network Properties", Journal of Applied Polymer Science, vol. 38, No. 11, (1989), pp. 2103–2113.
Heise et al, "Curing Mechanism and Thermal Properties of Epoxy–Imidazole Systems", Macromolecules, vol. 22, No. 1, (1989), pp. 99–104.
Laszlo et al, "Hardening Reactions of Epoxy–Phenol Systems in the Presence of Imidazole Type Catalysts by DSC", Angewandte Makromolekulare Chemie, vol. 172, (1989), pp. 37–45.
Lee et al, Handbook of Epoxy Resins, pp. 10–17, 1967.

(List continued on next page.)

Primary Examiner—Robert E. L. Sellers
(74) Attorney, Agent, or Firm—Lyon & Lyon LLP; James H. Shalek, Esq.; Kristin H. Neuman, Esq.

(57) ABSTRACT

Curable mixtures suitable for the manufacture of moldings, coatings and foams comprises a) an epoxy resin having more than one 1,2-epoxy group per molecule, b) as curing catalyst, an imidazole compound of formula I

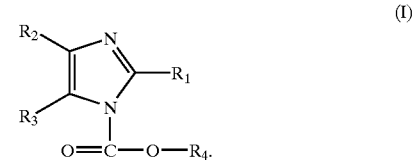

(I)

wherein $R_1$, $R_2$ and $R_3$ are each independently of the others a hydrogen atom, a halogen atom, alkyl having from 1 to 20 carbon atoms, alkoxy having from 1 to 20 carbon atoms, unsubstituted or halo-, nitro-, $C_{1-4}$alkyl- or $C_{1-4}$alkoxy-substituted aralkyl having from 7 to 20 carbon atoms, or unsubstituted or halo-, nitro-, $C_{1-4}$alkyl- or $C_{1-4}$alkoxy-substituted aryl having from 6 to 20 carbon atoms, and $R_4$ is alkyl having from 1 to 20 carbon atoms, alkenyl having from 2 to 20 carbon atoms, alkynyl having from 2 to 20 carbon atoms, unsubstituted or halo-, nitro-, $C_{1-4}$alkyl- or $C_{1-4}$alkoxy-substituted aralkyl having from 7 to 20 carbon atoms or unsubstituted or halo-, nitro-, $C_{1-4}$alkyl- or $C_{1-4}$alkoxy-substituted aryl having from 6 to 20 carbon atoms; and c) curing agent such as dicyadiamide or an anhydride.

3 Claims, No Drawings

OTHER PUBLICATIONS

Nishibuko et al., "Synthesis of Photoreactive Imidazole Derivatives and Thermal Curing Reaction of Epoxy Resins Catalyzed by Photo–Generated Imidazole," Polymer Journal, vol. 29, No. 5, 1997, The Society of Polymer Science, Japan, pp. 450–456.*

Chemical abstracts accession No. 1998:673628 for the Kawamura Rikagaku Kenkyusho Hokoku article by Nishikubo, pp. 1–15, 1997.*

Nishibuko et al., "Synthesis of Photoreactive Imidazole Derivatives and Thermal Curing Reaction of Epoxy Resins Catalyzed by Photo–Generated Imidazole," Polymer Journal, vol. 29, No. 5 (1997), pp. 450–456.*

Chemical abstracts accession No. 1998:673628 for the Kawamura Rikagaku Kenkyusho Hikoku article by Nishibuko (1997).*

Nishibuko et al., "Synthesis of Photoreactive Imidazola Derivatives and Thermal Curing Reaction of Epoxy Resin Catalyzed by Photo–Generated Imidazole," Polymer Journal, vol. 29, No. 5, 1997, The Society of Polymer Science, Japan, pp. 450–456.*

Chemical abstracts accession No. 1998:673628 for the Kawamura Rikagaku Kenkyusho Hokoku article by Nishibuko, pp. 1–15, 1997.*

Chem. Abstr. vol. 117, No. 17, (1992), 69658.*

Database Beilstein XP 002045014, abstr. for Bull. Soc. Chim, Belg., vol. 101, No. 2, (1982) pp. 147–158.*

Database Beilstein XP 002045016, abstr. for Kamijo et al., Chme. Pharm. Bu. II., vol. 31, No. 11, (1983), pp. 4189–4192.*

* cited by examiner

CURABLE MIXTURES BASED ON EPOXY RESINS COMPRISING IMIDAZOLES

This application is a division of Ser. No. 09/230,410 filed Jan. 25, 1999 now U.S. Pat. No. 6,174,985, which is a 371 of PCT/EP97/03811 filed Jul. 16, 1997.

The present invention relates to curable mixtures based on epoxy resins, which mixtures comprise an epoxy resin having more than one epoxy group per molecule and substituted imidazole compounds as curing catalyst or curing accelerator, and also to certain novel imidazole compounds.

The use of unsubstituted or substituted imidazole as a curing catalyst in the curing of epoxy resins is known. For example, H. Lee and K. Neville in "Handbook of Epoxy Resins", pages 10–17 (1967), report the property of epoxy resins cured with 2-ethyl-4-methyl-imidazole.

It has, surprisingly, been found that certain substituted imidazoles in admixture with epoxy resins have an even better latency at room temperature than mixtures of epoxy resins with imidazole or with 2-ethyl-4-imidazole, and at elevated temperature are distinguished by a high reactivity.

The present invention accordingly relates to novel curable mixtures comprising:
a) an epoxy resin having more than one 1,2-epoxy group per molecule and
b) as curing catalyst, an imidazole compound of formula I

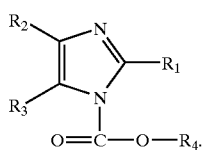

(I)

wherein $R_1$, $R_2$ and $R_3$ are each independently of the others a hydrogen atom, a halogen atom, alkyl having from 1 to 20 carbon atoms, alkoxy having from 1 to 20 carbon atoms, unsubstituted or halo-, nitro-, $C_{1-4}$alkyl- or $C_{1-4}$alkoxy-substituted aralkyl having from 7 to 20 carbon atoms, or unsubstituted or halo-, nitro-, $C_{1-4}$alkyl- or $C_{1-4}$alkoxy-substituted aryl having from 6 to 20 carbon atoms, and $R_4$ is alkyl having from 1 to 20 carbon atoms, alkenyl having from 2 to 20 carbon atoms, alkynyl having from 2 to 20 carbon atoms, unsubstituted or halo-, nitro-, $C_{1-4}$alkyl- or $C_{1-4}$alkoxy-substituted aralkyl having from 7 to 20 carbon atoms or unsubstituted or halo-, nitro, $C_{1-4}$alkyl- or $C_{1-4}$alkoxy-substituted aryl having from 6 to 20 carbon atoms. Suitable epoxy resins (a) for the preparation of the curable mixtures according to the invention are the epoxy resins customarily employed in epoxy resin technology. Examples of epoxy resins are:

I) Polyglycidyl and poly(β-methylglycidyl) esters, obtainable by reaction of a compound having at least two carboxy groups per molecule with epichlorohydrin or β-methyl-epichlorohydrin, respectively. The reaction is advantageously carded out in the presence of bases. An aliphatic polycarboxylic acid may be used as compound having at least two carboxy groups per molecule. Examples of such polycarboxylic acids are oxalic acid, succinic acid, glutaric acid, adipic acid, pimelic acid, suberic acid, azelaic acid and dimerised or trimerised linoleic acid. It is also possible, however, to use cycloaliphatic polycarboxylic acids, for example tetrahydrophthalic acid, 4-methyltetrahydrophthalic acid, hexahydrophthalic acid or 4-methylhexahydrophthalic acid. Aromatic polycarboxylic acids may also be used, for example phthalic acid, isophthalic acid or terephthalic acid.

II) Polyglycidyl or poly(β-methylglycidyl) ethers, obtainable by reaction of a compound having at least two free alcoholic hydroxy groups and/or phenolic hydroxy groups with epichlorohydrin or β-methylepichlorohydrin, respectively, under alkaline conditions, or in the presence of an acid catalyst with subsequent alkali treatment.

Such glycidyl ethers are derived, for example, from acyclic alcohols, such as from ethylene glycol, diethylene glycol and higher poly(oxyethylene) glycols, propane-1,2-diol or poly-(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and also polyepichlorohydrins. They may also, however, be derived, for example, from cycloaliphatic alcohols, for example 1,4-cyclohexanedimethanol, bis(4-hydroxycyclohexyl) methane or 2,2-bis(4-hydroxycyclohexyl)propane, or they have aromatic nuclei, such as N,N-bis(2-hydroxy-ethyl) aniline or p,p'-bis(2-hydroxyethylamino)diphenylmethane.

The glycidyl ethers may also be derived from mononuclear phenols, for example from resorcinol or hydroquinone, or are based on polynuclear phenols, for example bis(4-hydroxyphenyl)methane, 4,4'-dihydroxybiphenyl, bis(4-hydroxyphenyl)sulfone, 1,1,2,2-tetrakis(4-hydroxyphenyl)ethane, 2,2-bis(4-hydroxyphenyl) propane, 2,2-bis(3,5-dibromo-4-hydroxyphenyl)propane, or from novolaks, obtainable by condensation of aldehydes, for example formaldehyde, acetaldehyde, chloral or furfuraldehyde, with phenols, such as phenol, or with phenols that are substituted in the nucleus by chlorine atoms or by $C_1$–$C_9$alkyl groups, for example 4-chlorophenol, 2-methylphenol or 4-tert-butylphenol, or by condensation with bisphenols, for example those of the type mentioned above.

III) Poly(N-glycidyl) compounds, obtainable by dehydrochlorination of the reaction products of epichlorohydrin with amines that contain at least two amine hydrogen atoms. The amines are, for example, aniline, n-butylamine, bis(4-aminophenyl)methane, m-xylylenediamine or bis(4-methylaminophenyl)methane.

The poly(N-glycidyl) compounds, however, also include triglycidyl isocyanurate, N,N'-di-glycidyl derivatives of cycloalkyleneureas, such as ethyleneurea or 1,3-propyleneurea, and diglycidyl derivatives of hydantoins, such as 5,5-dimethythydantoin.

IV) Poly(S-glycidyl) compounds, for example di-S-glycidyl derivatives that are derived from dithiols, for example ethane-1,2-dithiol or bis(4-mercaptomethylphenyl) ether.

V) Cycloaliphatic epoxy resins, for example bis(2,3-epoxycyclopentyl) ethers, 2,3-epoxycyclopentylglycidyl ether, 1,2-bis(2,3-epoxycyclopentyloxy)ethane or 3,4-epoxycyclohexylmethyl-3',4'-epoxycyclohexanecarboxylate.

It is also possible, however, to use epoxy resins in which the 1,2-epoxy groups are bonded to different hetero atoms or functional groups; those compounds include, for example, the N,N,O-triglycidyl derivative of 4-aminophenol, glycidyl ethers/glycidyl esters of salicylic acid, N-glycidyl-N'-(2-glycidyloxypropyl)-5,5-dimethylhydantoin and 2-glycidyloxy-1,3-bis(5,5-dimethyl-1-glycidylhydantoin-3-yl)propane.

For the preparation of the epoxy resin compositions according to the invention it is preferred to use a liquid or solid polyglycidyl ether or ester, especially a liquid or solid diglycidyl ether of bisphenol or a solid or liquid diglycidyl ester of a cycloaliphatic or aromatic dicarboxylic acid, or a cycloaliphatic epoxy resin. It is also possible to use mixtures of epoxy resins.

Suitable solid polyglycidyl ethers and esters are compounds having melting points from above room temperature up to approximately 250° C. Preferably, the melting points of the solid compounds are in the range from 50 to 150° C. Such solid compounds are known and some of them are available commercially. As solid polyglycidyl ethers and esters it is also possible to use the advancement products obtained by pre-extension of liquid polyglycidyl ethers and esters.

The epoxy resin compositions according to the invention especially comprise a liquid polyglycidyl ether or ester.

The curable mixtures according to the invention comprise as component (b) preferably imidazole compounds of formula I wherein $R_1$ and $R_2$ are each independently of the other a hydrogen atom, a halogen atom, alkyl having from 1 to 6 carbon atoms, alkoxy having from 1 to 6 carbon atoms or phenyl, $R_3$ is a hydrogen atom or phenyl, and $R_4$ is alkyl having from 1 to 10 carbon atoms, alkenyl having from 2 to 10 carbon atoms, unsubstituted or substituted phenyl or unsubstituted or substituted benzyl.

Suitable single or multiple substituents of phenyl or of benzyl are halogen atoms and nitro, $C_1$–$C_4$alkyl- and $C_1$–$C_4$alkoxy groups.

The mixtures according to the invention especially comprise as component (b) an imidazole compound of formula I wherein each of $R_1$ and $R_3$ is a hydrogen atom.

$R_2$ is phenyl, and $R_4$ is alkenyl having from 2 to 10 carbon atoms, or unsubstituted or substituted phenyl or unsubstituted or substituted benzyl, or wherein $R_1$ is branched alkyl having from 3 to 6 carbon atoms, each of $R_2$ and $R_3$ is a hydrogen atom, and $R_4$ is unsubstituted or substituted phenyl, unsubstituted or substituted benzyl or branched alkyl having from 3 to 6 carbon atoms.

In an especially preferred embodiment, the mixtures according to the invention comprise an imidazole compound of the formula

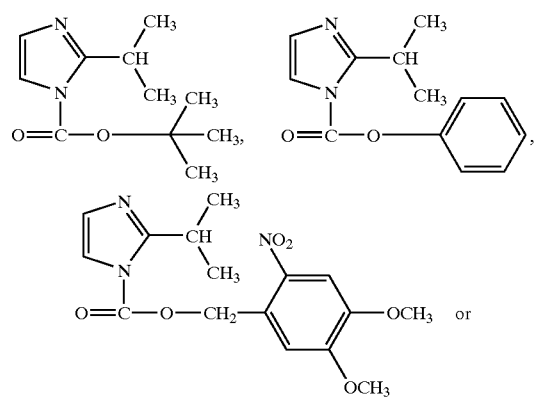

-continued

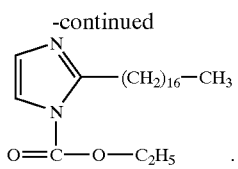

In the curable mixtures according to the invention, the proportion of component (b) is generally from 0.1 to 20% by weight, preferably from 1 to 15% by weight, based on the amount of component (a).

Some of the compounds of formula I are known compounds, which are described, for example, in U.S. Patent Specification U.S. Pat. No. 4,189,543 and can be prepared by reacting 1.) 1 mol of an imidazole compound of the formula

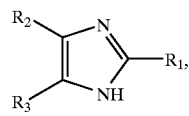

wherein $R_1$, $R_2$ and $R_3$ are as defined for formula I, with 1 mol of a chloroformic acid ester of the formula

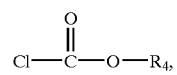

wherein $R_4$ is as defined for formula I, or

2.) 1 mol of an imidazole compound of the formula

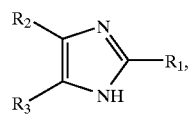

wherein $R_1$, $R_2$ and $R_3$
are as defined for formula I, with 1 mol of a dicarbonate of the formula

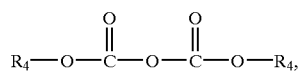

wherein $R_4$ is as defined for formula I, or

3.) 1 mol of a carbonyldiimidazole compound of the formula

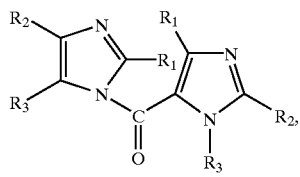

wherein $R_1$, $R_2$ and $R_3$ are as defined for formula I, with 1 mol of an alcohol of the formula

$R_4$—OH wherein $R_4$ is as defined for formula I, to form compounds of formula I.

Insofar as the compounds of formula I are novel compounds, protection is also claimed for those compounds.

The present invention accordingly relates also to novel imidazole compounds of formula II

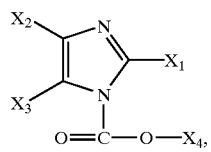

wherein $X_1$, $X_2$ and $X_3$ are each independently of the others a hydrogen atom, a halogen atom, alkyl having from 1 to 20 carbon atoms, alkoxy having from 1 to 20 carbon atoms, unsubstituted or halo-, nitro-, $C_{1-4}$alkyl- or $C_{1-4}$alkoxy-substituted aralkyl having from 7 to 20 carbon atoms, or unsubstituted or halo-, nitro-, $C_{1-4}$alkyl- or $C_{1-4}$alkoxy-substituted aryl having from 6 to 20 carbon atoms, and X4 is alkenyl having from 10 to 20 carbon atoms or alkenyl having from 2 to 20 carbon atoms, or wherein each of $X_1$ and $X_3$ is a hydrogen atom, $X_2$ is unsubstituted or halo-, nitro-, $C_{1-4}$alkyl- or $C_{1-4}$alkoxy-substituted aryl having from 6 to 20 carbon atoms, and $X_4$ is alkenyl or aryl, or wherein $X_1$ is branched alkyl having from 2 to 6 carbon atoms, each of $X_2$ and $X_3$ is a hydrogen atom, and $X_4$ is aryl or branched alkyl having from 2 to 6 carbon atoms.

In formula II, preferably each of $X_1$ and $X_3$ is a hydrogen atom, $X_2$ is phenyl, and $X_4$ is alkenyl having from 2 to 6 carbon atoms or unsubstituted or halo-, nitro-, $C_{1-4}$alkyl- or $C_{1-4}$alkoxy-substituted aryl having from 6 to 20 carbon atoms, or $X_1$ is branched alkyl having from 3 to 6 carbon atoms, each of $X_2$ and $X_3$ is a hydrogen atom, and $X_4$ is unsubstituted or halo-, nitro-, $C_{1-4}$alkyl- or $C_{1-4}$alkoxy-substituted aryl having from 6 to 20 carbon atoms or branched alkyl having from 2 to 6 carbon atoms.

In formula II, especially $X_1$ is branched alkyl having from 3 to 6 carbon atoms each of $X_2$ and $X_3$ is a hydrogen atom, and $X_4$ is unsubstituted or halo-, nitro-, $C_{1-4}$alkyl- or $C_{1-4}$alkoxy-substituted phenyl, unsubstituted or halo-, nitro-, $C_{1-4}$alkyl- or $C_{1-4}$alkoxy-substituted benzyl or branched alkyl having from 3 to 6 carbon atoms.

Especially preferred are the imidazole compounds of the formulae

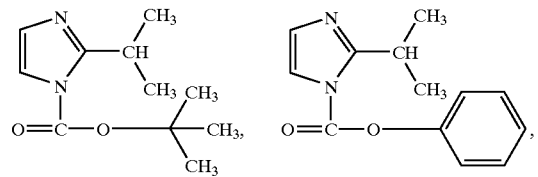

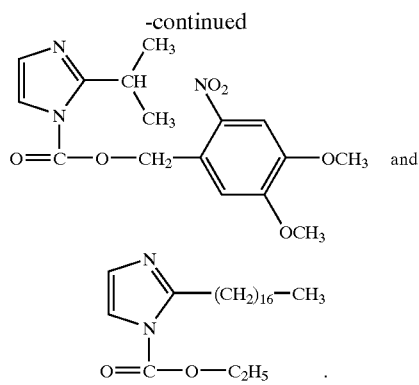

The compounds of formula 11 may also be prepared in accordance with the three above-mentioned processes using the appropriate starting materials.

As mentioned at the outset, the imidazole compounds of formulae I and II are also suitable as curing accelerators in mixtures comprising epoxy resin and curing agent.

The present invention accordingly relates also to curable mixtures comprising a) an epoxy compound having more than one 1,2-epoxy group per molecule, b1) as curing accelerator, an imidazole compound of formula I

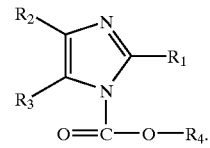

wherein $R_1$, $R_2$ and $R_3$ are each independently of the others a hydrogen atom, a halogen atom, alkyl having from 1 to 20 carbon atoms, alkoxy having from 1 to 20 carbon atoms, unsubstituted or halo-, nitro-, $C_{1-4}$alkyl- or $C_{1-4}$alkoxy-substituted aralkyl having from 7 to 20 carbon atoms, or unsubstituted or halo-, nitro-, $C_{1-4}$alkyl- or $C_{1-4}$alkoxy-substituted aryl having from 6 to 20 carbon atoms, and $R_4$ is alkyl having from 1 to 20 carbon atoms, alkenyl having from 2 to 20 carbon atoms, alkynyl having from 2 to 20 carbon atoms, unsubstituted or halo-, nitro-, $C_{1-4}$alkyl- or $C_{1-4}$alkoxy-substituted aralkyl having from 7 to 20 carbon atoms or unsubstituted or halo-, nitro-, $C_{1-4}$alkyl- or $C_{1-4}$alkoxy-substituted aryl having from 6 to 20 carbon atoms, and c) a curing agent for epoxy resins.

As curing accelerator it is preferred to use the same imidazole compounds of formula I preferably used as curing catalyst. There is also used as curing accelerator generally from 0.1 to 20% by weight of imidazole compound of formula I, based on the amount of component (a).

The curable mixtures according to the invention may comprise as curing agent (c) a curing agent customarily employed in epoxy resin technology, for example dicyandiamide, polycarboxylic acids and anhydrides thereof, polyamines, polyaminoamides, amino group-containing adducts, aliphatic or aromatic polyols or catalytically active curing agents.

The mixtures according to the invention preferably comprise as curing agent dicyandiamide, a polycarboxylic acid or an anhydride thereof.

There may be mentioned as suitable polycarboxylic acids, for example, aliphatic polycarboxylic acids, for example maleic acid, oxalic acid, succinic acid, nonyl- or dodecylsuccinic acid, glutaric acid, adipic acid, pimelic acid, suberic acid, azelaic acid and dimerised or trimerised linoleic acid, cycloaliphatic polycarboxylic acids, for example tetrahydrophthalic acid, methylendomethylenetetrahydrophthalic acid, hexachloroendomethylenetetrahydrophthalic acid, 4-methyltetrahydrophthalic acid, hexahydrophthalic acid and 4-methylhexahydrophthalic acid, and aromatic polycarboxylic acids, for example phthalic acid, isophthalic acid, terephthalic acid, trimellitic acid, pyromellitic acid and benzophenone-3,3',4,4'-tetracarboxylic acid, and the anhydrides of the mentioned polycarboxylic acids.

The amount of curing agent used depends upon the chemical nature of the curing agent and upon the desired properties of the curable mixture and of the cured product. The maximum amount can be determined readily. When the curing agent is an amine, usually from 0.75 to 1.25 equivalents of amine hydrogen are used per equivalent of epoxide. When polycarboxylic acids or anhydrides thereof are used, usually from 0.4 to 1.1 equivalents of carboxy group or anhydride group, respectively, are used per equivalent of epoxide. When polyphenols are used as curing agent, from 0.75 to 1.25 phenolic hydroxy groups are used per equivalent of epoxide. Catalytically active curing agents are generally used in amounts of from 1 to 40 parts by weight per 100 parts by weight of epoxy resin.

The curable mixtures according to the invention may also comprise the fillers and reinforcing materials customarily employed in epoxy resin technology. Suitable fillers include, for example: mineral and fibrous fillers, such as quartz powder, fused silica, aluminium oxide, glass powder, mica, kaolin, dolomite, graphite, carbon black, and also carbon fibres and textile fibres. Preferred fillers are quartz powder, fused silica, aluminium oxide and dolomite. Suitable reinforcing materials are, for example, glass fibres or carbon fibres.

The curable mixtures according to the invention are prepared according to methods known per se, for example using known mixing apparatus, for example stirrers, kneaders, rollers or, in the case of solid substances, dry mixers.

The curing of the curable mixtures according to the invention to form mouldings, coatings or the like is carried out in a manner customarily employed in epoxy resin technology, as described, for example, in "Handbook of Epoxy Resins", 1967, by H. Lee and K.Neville.

The curable mixtures according to the invention are excellently suitable as casting resins, laminating resins, adhesives, compression moulding compounds, foamed materials, coating compounds and also as encasing systems for electrical and electronic components, especially as laminating resins or foamed materials.

The present invention accordingly relates also to the moulded materials, coatings or bonded materials manufactured from the curable mixtures according to the invention.

The following Examples describe the preparation of compounds of formulae I and II; the yields of the compounds have not been optimised.

EXAMPLE A1

9.45 g (0.1 mol) of chloroformic acid methyl ester are added dropwise in portions to a solution, cooled to from 0 to 5° C. using an ice-water bath, of 13.6 g (0.2 mol) of imidazole in 200 ml of tetrahydrofuran, the portions being such that the temperature of the reaction solution remains below 5° C. Once the addition is complete, the ice-water bath is removed so that the reaction solution can warm up to room temperature. The white precipitate is filtered off, and the filtrate is concentrated to dryness by evaporation to yield 11.8 g (94% of the theoretical yield) of the compound of the formula

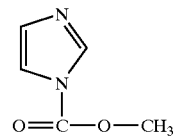

having a melting point of 41.8° C.

Elemental Analysis:

| found | calculated |
|---|---|
| 47.27% C | 47.62% C |
| 4.83% H | 4.80% H |
| 22.14% N | 22.21% N. |

EXAMPLE A2

10.85 g (0.1 mol) of chloroformic acid ethyl ester are added dropwise in portions, with stirring, to a mixture, cooled to below 5° C. using an ice-water bath, of 6.80 g (0.1 mol) of imidazole and 11.1 g (0.11 mol) of triethylamine in 100 ml of acetonitrile, the portions being such that the temperature of the reaction mixture remains below 5° C. The reaction mixture is then stirred at that temperature for a further hour. The reaction mixture is then allowed to warm up to room temperature, and the resulting white precipitate is filtered off and washed with acetonitrile. The filtrate is concentrated to dryness by evaporation, and the residue is taken up in dichloromethane. The organic phase is washed three times with water and then dried over $Na_2SO_4$. After filtration, the organic phase is concentrated to dryness by evaporation in vacuo to yield 11.6 g (82% of the theoretical yield) of the compound of the formula

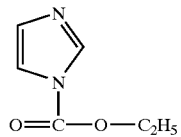

in the form of a colourless liquid.

Elemental Analysis:

| found | calculated |
|---|---|
| 51.16% C | 51.42% C |
| 5.78% H | 5.75% H |
| 19.70% N | 19.99% N. |

EXAMPLE A3

The compound of the formula

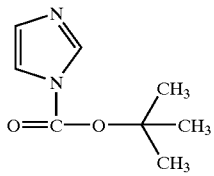

is available commercially (Lancaster).
Melting point: 46–47° C.

EXAMPLE A4

The process set out in Example 2 is repeated using chloroformic acid n-butyl ester instead of chloroformic acid ethyl ester to yield the compound of the formula

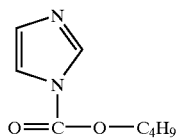

Yield: 85% of the theoretical yield.
Elemental Analysis:

| found | calculated |
| --- | --- |
| 56.89% C | 57.13% C |
| 7.24% H | 7.19% H |
| 16.49% N | 16.66% N. |

EXAMPLE A5

The process set out in Example 2 is repeated using chloroformic acid n-octyl ester instead of chloroformic acid ethyl ester to yield the compound of the formula

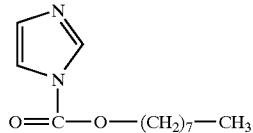

having a melting point of 39.1° C.
Yield: 98% of the theoretical yield.

EXAMPLE A6

A mixture of 4 g (25 mmol) of N,N'-carbonyldiimidazole and 6.3 g of 1-heptadecanol in 100 ml of tetrahydrofuran is stirred overnight at room temperature. After removal of the solvent by evaporation, the solid residue is triturated in hexane and insoluble residue is removed by filtration. The filtrate is concentrated to dryness by evaporation to yield 8.0 g (92% of the theoretical yield) of a solid white crystalline substance having a melting point of 59.3° C. that corresponds to the formula

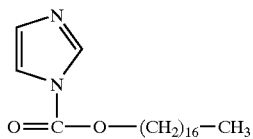

Elemental Analysis:

| found | calculated |
| --- | --- |
| 72.69% C | 71.95% C |
| 11.11% H | 10.93% H |
| 7.23% N | 7.99% N. |

The $^1$H NMR spectrum of the prepared compound corresponds to the formula given above.

EXAMPLE A7

3.96 g (29.4 mmol) of chloroformic acid buten-3-yl ester are added dropwise, with stirring, to a mixture, maintained at below 5° C. using an ice-water bath, of 2 g (29.4 mmol) of imidazole and 3.27 g (32.3 mmol) of triethylamine in 50 ml of acetonitrile, in such amounts that the reaction temperature remains below 5° C. Overnight the reaction mixture is stirred further at room temperature, and then the white precipitate is filtered off and washed with acetonitrile. The filtrate is concentrated to dryness, the residue is dissolved in dichloromethane, and the organic phase is washed three times with water. The organic phase is then dried over $Na_2SO_4$, filtered, and concentrated by evaporation in vacuo at 40° C. 4.4 g (90% of the theoretical yield) of a pale-yellow liquid are obtained that corresponds to the formula

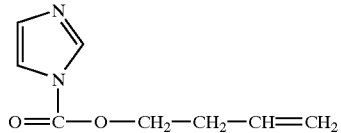

Elemental Analysis:

| found | calculated |
| --- | --- |
| 57.60% C | 57.82% C |
| 6.11% H | 6.07% H |
| 16.72% N | 16.86% N. |

The $^1$H NMR spectrum of the prepared compound corresponds to the formula given above.

EXAMPLE A8

A mixture of 4 g (25 mmol) of N,N'-carbonyidiimidazole and 2.12 g (25 mmol) of 2-methyl-3-buten-2-ol in 50 ml of dichloromethane is stirred overnight at room temperature. After removal of the solvent by evaporation, the solid residue is triturated in 10 ml of hexane and filtered to remove insoluble residue which is washed with 40 ml of hexane. The filtrate is concentrated to dryness by evaporation yielding 2.64 g of the crude imidazole compound which is separated off by chromatography over 60 g of silica gel using ethyl acetate as eluant, the first 10 fractions being concentrated by evaporation to yield 1.74 g (39% of the theoretical yield) of the pure compound of the formula

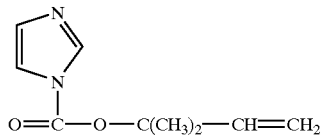

Elemental Analysis:

| found | calculated |
| --- | --- |
| 59.95% C | 60.00% C |
| 6.85% H | 6.67% H |
| 15.33% N | 15.55% N. |

The $^1$H NMR spectrum of the prepared compound corresponds to the formula given above.

EXAMPLE A9

In accordance with the process given in Polymer Journal, Vol. 26, No. 7, pages 864–867, 5.35 g (35 mmol) of N,N'-carbonyidiimidazole and 5.7 g (35 mmol) of 2-nitrobenzyl alcohol in 140 ml of acetonitrile are stirred overnight at room temperature. After filtering off the precipitate, the filtrate is concentrated to dryness by evaporation to yield 4.6 g (68.5% of the theoretical yield) of a compound of the formula

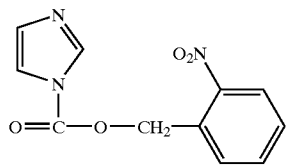

having a melting point of 141.3° C.
Elemental Analysis:

| found | calculated |
| --- | --- |
| 53.38% C | 53.44% C |
| 3.77% H | 3.67% H |
| 16.98% N | 17.00% N. |

EXAMPLE A10

3.00 g (10.7 mmol) of chloroformic acid 6-nitroveratryl ester are added in portions, with stirring, to a mixture, maintained at below 3° C. using an ice-water bath, of 0.74 g (10.7 mmol) of imidazole and 1.21 g (11.9 mmol) of triethylamine in 100 ml of acetonitrile, the portions being such that the reaction temperature remains below 10° C. Overnight the mixture is stirred further at room temperature, and then the white precipitate is filtered off and washed with acetonitrile. The filtrate is concentrated to dryness, the residue is dissolved in dichloromethane and the organic phase is washed three times with water. The organic phase is dried over Na2SO, filtered and concentrated by evaporation. The crude product is recrystallised from xylene to yield 2.71 g (81% of the theoretical yield) of slightly orange-coloured needles that correspond to the formula

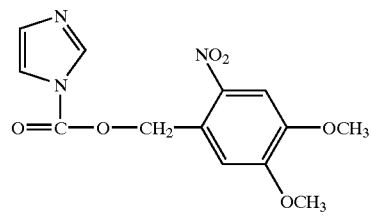

and have a melting point of 136.1° C.
Elemental Analysis:

| found | calculated |
| --- | --- |
| 51.17% C | 50.82% C |
| 4.60% H | 4.26% H |
| 13.23% N | 13.68% N |

The $^1$H NMR spectrum of the prepared compound corresponds to the formula given above.

EXAMPLE A11

5.42 g (50 mmol) of chloroformic acid ethyl ester are added dropwise in portions, with stirring, to a solution, maintained at below 3° C. using an ice-water bath, of 7.2 g (50 mmol) of 4-phenylimidazole and 5.56 g (55 mmol) of triethylamine in a solvent mixture of 50 ml of acetonitrile and 40 ml of dichloromethane, the portions being such that the temperature of the reaction solution remains below 5° C. After further stirring at that temperature for 30 minutes, the ice-water bath is removed, and the reaction solution warms up to room temperature. The beige precipitate is filtered off, and dichloromethane is added to the filtrate. The organic phase is washed three times with water and dried over $Na_2SO_4$. After filtration, the organic phase is concentrated to dryness by evaporation. The resulting crude product is recrystallised from cyclohexane to yield 9.7 g (90% of the theoretical yield) of the pure compound of the formula

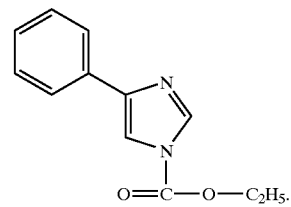

The white crystals have a melting point of 110.9° C.
Elemental Analysis:

| found | calculated |
| --- | --- |
| 66.63% C | 66.65% C |
| 5.78% H | 5.59% H |
| 12.99% N | 12.96% N. |

The $^1$H NMR spectrum of the prepared compound corresponds to the formula given above.

EXAMPLE A12

1.9 g (13.9 mmol) of chloroformic acid n-butyl ester are added dropwise in portions, with stirring, to a solution, maintained at below 4° C. using an ice-water bath, of 2.0 g (13.9 mmol) of 4-phenylimidazole and 1.55 g (15.3 mmol) of triethylamine in a solvent mixture of 70 ml of acetonitrile, 50 ml of ether and 120 ml of tert-butyl methyl ether, the portions being such that the temperature of the reaction solution remains below 5° C. After further stirring at that temperature for 1 hour, the ice-water bath is removed, and the reaction solution is allowed to warm up to room temperature. The white precipitate is filtered off, and the filtrate is concentrated to dryness by evaporation. The crude product is purified by chromatography over silica gel using dichloromethane/ethyl acetate (30:1) as eluant. The first three fractions (75 ml) are concentrated to dryness by evaporation to yield 2.8 g (83% of the theoretical yield) of a pure compound of the formula

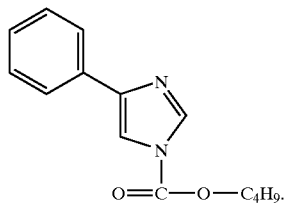

The white crystals have a melting point of 11 6.9° C.

Elemental Analysis:

| found | calculated |
|---|---|
| 68.64% C | 68.83% C |
| 6.77% H | 6.60% H |
| 11.35% N | 11.47% N. |

The $^1$H NMR spectrum of the prepared compound corresponds to the formula given above.

EXAMPLE A13

2.69 g (20 mmol) of chloroformic acid buten-3-yl ester are added dropwise in portions, with stirring, to a solution, maintained at below 3° C. using an ice-water bath, of 2.88 g (20 mmol) of 4-phenylimidazole and 2.22 g (22 mmol) of triethylamine in 100 ml of acetonitrile, the portions being such that the temperature of the reaction solution remains below 5° C. The ice-water bath is removed, and the reaction solution is allowed to warm up to room temperature and is stirred further overnight. The white precipitate is filtered off, and the filtrate is concentrated to dryness by evaporation. The residue is dissolved in dichloromethane and washed three times with water. The organic phase is dried over Na$_2$SO$_4$, filtered and concentrated to dryness by evaporation. The residue is triturated in 100 ml of hexane, filtered to remove insoluble material, and the filtrate is dried in a vacuum oven. 3.67 g (76% of the theoretical yield) of a pure compound of the formula

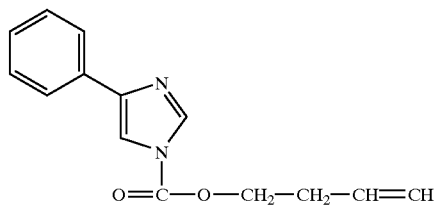

are obtained in the form of a white substance that melts at 79.3° C.

Elemental Analysis:

| found | calculated |
|---|---|
| 69.33% C | 69.34% C |
| 5.81% H | 5.78% H |
| 11.56% N | 11.56% N. |

The $^1$H NMR spectrum of the prepared compound corresponds to the formula given above.

EXAMPLE A14

1.5 g (8.8 mmol) of chloroformic acid benzyl ester are added dropwise in portions, with stirring, to a suspension, maintained at below 5° C. using an ice-water bath, of 1.0 g (8.8 mmol) of 4-phenylimidazole in a solvent mixture of 15 ml of acetonitrile and 3 ml of dichloromethane, the portions being such that the temperature of the reaction solution remains below 5° C. The reaction solution is stirred at that temperature for a further hour and then the ice-water bath is removed, and the reaction solution is allowed to warm up to room temperature and is then stirred for a further 45 minutes. After removal of the solvent and after the addition of water, the product is extracted using dichloromethane. The organic phase is washed three times with water and dried over Na$_2$SO$_4$, filtered and concentrated to dryness by evaporation. The residue is triturated in 100 ml of hexane and filtered to remove insoluble material, and the filtrate is dried in a vacuum oven. 1.53 g of a crude product are obtained, which are recrystallised from a solvent mixture of dichloromethane and hexane. 1.21 g (56% of the theoretical yield) of a pure compound of the formula

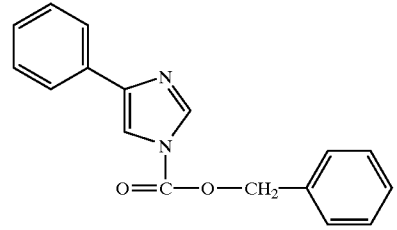

are obtained in the form of a white flocculent substance that melts at 93.7° C.

Elemental Analysis:

| found | calculated |
|---|---|
| 73.33% C | 73.37% C |
| 5.23% H | 5.07% H |
| 9.88% N | 10.07% N. |

The $^1$H NMR spectrum of the prepared compound corresponds to the formula given above.

EXAMPLE A15

1.37 g (8.8 mmol) of chloroformic acid phenyl ester are added dropwise in portions, with stirring, to a suspension of 1.0 g (8.8 mmol) of 4-phenylimidazole and 1.0 g (9.6 mmol) of triethylamine in a solvent mixture consisting of 15 ml of acetonitrile and 5 ml of dichloro-methane, the portions being such that the temperature of the reaction solution remains below 20° C. The reaction solution is then stirred at room temperature for a further hour, the white precipitate is filtered off and the filtrate is concentrated to dryness by evaporation. Water is added to the residue and extraction is carried out in dichloromethane. The organic phase is washed several times with water, filtered, dried over $Na_2SO_4$ and concentrated to dryness by evaporation. 1.9 g (93% of the theoretical yield) of a pure compound of the formula

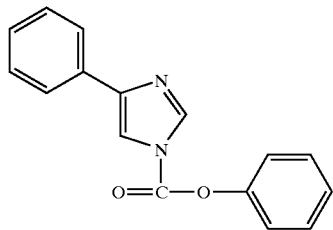

are obtained in the form of a white powder that melts at 138.1° C.
Elemental Analysis:

| found | calculated |
|---|---|
| 72.48% C | 72.72% C |
| 4.58% H | 4.58% H |
| 10.70% N | 10.60% N. |

The $^1$H NMR spectrum of the prepared compound corresponds to the formula given above.

EXAMPLE A16

5.32 g (50 mmol) of chloroformic acid vinyl ester are added dropwise in portions, with stirring, to a suspension, maintained at below 4° C. using an ice-water bath, of 7.21 g (50 mmol) of 4-phenylimidazole and 5.56 g (55 mmol) of triethylamine in a solvent mixture of 170 ml of acetonitrile and 300 ml of tert-butyl methyl ether, the portions being such that the temperature of the reaction solution remains below 5° C. The ice-water bath is removed, and the reaction solution is allowed to warm up to room temperature and is then stirred at room temperature for a further 24 hours. The white precipitate is filtered off, and the filtrate is washed several times with water. The organic phase is dried over $Na_2SO_4$, filtered and concentrated to dryness by evaporation. 6.16 g (58% of the theoretical yield) of a pure compound of the formula

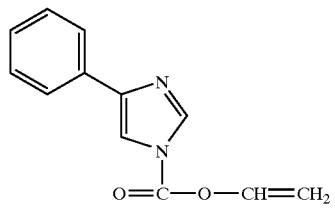

are obtained in the form of colourless needles having a melting point of 128.1° C.
Elemental Analysis:

| found | calculated |
|---|---|
| 67.25% C | 67.28% C |
| 4.78% H | 4.71% H |
| 13.06% N | 13.08% N. |

The $^1$H NMR spectrum of the compound obtained corresponds to the formula given above.

EXAMPLE A17

10.78 g (50 mmol) of chloroformic acid 4-nitrobenzyl ester are added dropwise in portions, with stirring, to a solution, maintained at below 3° C. using an ice bath, of 7.21 g (50 mmol) of 4-phenylimidazole and 5.57 g (55 mmol) of triethylamine in 500 ml of tert-butyl methyl ether, the portions being such that the temperature of the reaction solution remains below 3° C. The ice bath is removed, and the reaction solution is allowed to warm up to room temperature and is then stirred further overnight. The white precipitate is filtered off and the filtrate is washed five times with water and dried over $Na_2SO_4$. The slightly yellow solid substance obtained after concentration to dryness by evaporation is recrystallised from toluene. 1.01 g (6% of the theoretical yield) of a pure compound of the formula

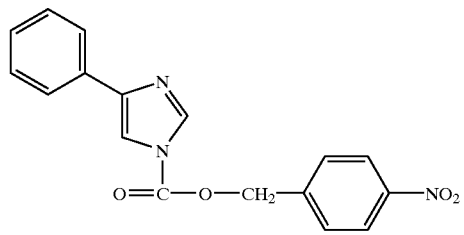

are obtained having a melting point of 1 55.0° C.
Elemental Analysis:

| found | calculated |
|---|---|
| 63.29% C | 63.15% C |
| 4.47% H | 4.36% H |
| 12.83% N | 12.99% N. |

The $^1$H NMR spectrum of the compound obtained corresponds to the formula given above.

EXAMPLE A18

1.94 g (7 mmol) of chloroformic acid 6-nitroveratryl ester are added in portions, with stirring, to a solution, maintained at below 4° C. using an ice-water bath, of 1.01 g (7 mmol) of 4-phenylimidazole and 0.78 g (7 mmol) of triethylamine in 90 ml of acetonitrile, the portions being such that the temperature of the reaction solution remains below 5° C. The ice-water bath is removed, and the reaction solution is allowed to warm up to room temperature and is then stirred at room temperature for a further 2 hours. After filtration of the resulting yellow suspension, the solvent is evaporated off from the filtrate, and the residue is dissolved in 100 ml of dichloromethane. The organic phase is washed three times with water, dried over $Na_2SO_4$ and concentrated to dryness by evaporation. 2.27 g (84% of the theoretical yield) of a pure compound of the formula

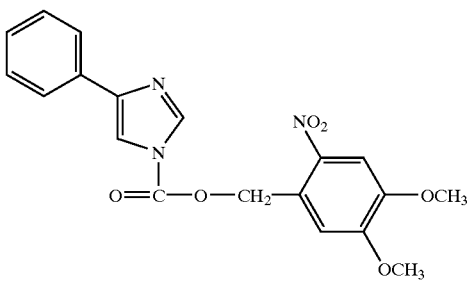

are obtained in the form of a solid yellow substance having a melting point of 188.3° C.
Elemental Analysis:

| found | calculated |
|---|---|
| 59.51% C | 59.47% C |
| 4.51% H | 4.43% H |
| 10.94% N | 10.96% N. |

The $^1$H NMR spectrum of the compound obtained corresponds to the formula given above.

EXAMPLE A19

The process set out in Example 2 is repeated using 2-phenylimidazole instead of imidazole, and a compound of the formula

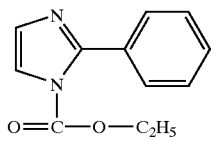

is obtained.
Yield: 21% of the theoretical yield.
Elemental Analysis:

| found | calculated |
|---|---|
| 66.59% C | 66.65% C |
| 5.67% H | 5.59% H |
| 12.95% N | 12.96% N. |

EXAMPLE A20

156.5 g (1 mol) of chloroformic acid phenyl ester are added dropwise in portions to a stirred solution of 188.18 g (1 mol) of 2-phenylimidazole and 1111.31 g (1.1 mol) of triethylamine in a solvent mixture of 1 liter of acetonitrile and 1.3 liters of dichloromethane, the portions being such that the temperature of the reaction solution, cooled using an ice-water bath, remains between 15° C. and 20° C. The reaction solution is then stirred at room temperature for a further 48 hours. After filtration of the precipitate, the solvent is evaporated off from the filtrate, and the residue is dissolved in dichloromethane. The organic phase is washed three times with water, dried over $Na_2SO_4$ and concentrated to dryness by evaporation. 257.6 g of a crude product that still contains small amounts of unreacted 2-phenylimidazole are obtained. The crude product is recrystallised from tert-butyl methyl ether to yield 131.1 g (49% of the theoretical yield) of a pure compound of the formula

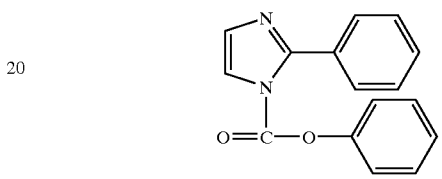

in the form of colourless needles that melt at 188.3° C.

Elemental Analysis:

| found | calculated |
|---|---|
| 72.61% C | 72.72% C |
| 4.71% H | 4.58% H |
| 10.65% N | 10.60% N. |

The $^1$H NMR spectrum of the compound obtained corresponds to the formula given above.

EXAMPLE A21

119.3 g (1.1 mol) of chloroformic acid ethyl ester are added dropwise in portions, with stirring, to a suspension, maintained at below 3° C. using an ice-water bath, of 158.2 g (1 mol) of 4-methyl-2-phenylimidazole and 112.1 g (1.1 mol) of,triethylamine in 4 liters of tetrahydrofuran, the portions being such that the temperature of the reaction solution remains below 5° C. The ice-water bath is removed, and the reaction solution is allowed to warm up to room temperature and is then stirred at room temperature overnight. The white precipitate is filtered off, and the filtrate is concentrated to dryness. The residue is taken up in 1 liter of dichloromethane, and the organic phase is washed three times with water and then dried over $Na_2SO_4$, filtered and concentrated to dryness by evaporation. The residue is triturated in hexane and filtered, and the filtrate is concentrated to dryness again, yielding a red-orange liquid which is purified by chromatography over silica gel using a solvent mixture of 7 parts of ethylacetate and 3 parts of acetonitrile as eluant. Evaporation of the fractions 8 to 21 (150 ml) yields 119.6 g (52% of the theoretical yield) of a pure compound of the formula

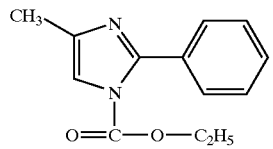

in the form of an orange liquid.
Elemental Analysis

| found | calculated |
|---|---|
| 67.73% C | 67.81% C |
| 6.28% H | 6.13% H |
| 12.17% N | 12.17% N. |

The ¹H NMR spectrum of the compound obtained corresponds to the structural formula given above.

EXAMPLE A22

The process set out in Example 2 is repeated using 2-ethyl-4-methylimidazole instead of imidazole and a compound of the formula

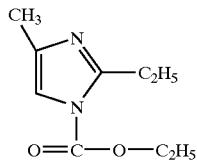

is obtained.
Yield: 77% of the theoretical yield.
Elemental Analysis:

| found | calculated |
|---|---|
| 58.93% C | 59.32% C |
| 7.86% H | 7.74% H |
| 15.30% N | 15.37% N. |

EXAMPLE A23

15.65 g (0.1 mol) of chloroformic acid phenyl ester are added dropwise in portions, with stirring, to a solution, maintained at below 2° C. using an ice-water bath, of 11.0 g (0.1 mol) of 2-ethyl-4-methylimidazole and 11.13 g (0.11 mol) of triethylamine in 100 ml of acetonitrile, the portions being such that the temperature of the reaction solution remains below 5° C. The ice-water bath is removed, and the reaction solution is allowed to warm up to room temperature and is then stirred at room temperature for a further 1.5 hours. The precipitate is filtered off and washed with dichloromethane, and the substance is isolated from the filtrate by extraction. The organic phase is washed three times with water, dried over Na₂SO₄ and concentrated to dryness by evaporation. A yellow solid substance is obtained, which is recrystallised from hexane to yield 17.2 g (75% of the theoretical yield) of a pure compound of the formula

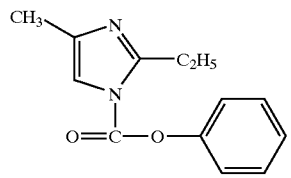

in the form of slightly yellow needles having a melting point of 188.3° C.
Elemental Analysis:

| found | calculated |
|---|---|
| 67.63% C | 67.81% C |
| 6.21% H | 6.13% H |
| 12.21% N | 12.17% N. |

The ¹H NMR spectrum of the compound obtained corresponds to the formula given above.

EXAMPLE A24

170.6 g (1 mol) of chloroformic acid benzyl ester are added dropwise in portions, with stirring, to a solution, maintained at below 3° C. using an ice-water bath, of 110.16 g (1 mol) of 2-ethyl-4-methylimidazole and 111.3 g (1.1 mol) of triethylamine in 1.5 liters of acetonitrile, the portions being such that the temperature of the reaction solution remains below 5° C. The ice-water bath is removed, and the reaction solution is allowed to warm up to room temperature and is then stirred at room temperature for a further 3 hours. The precipitate is filtered off, and the filtrate is extracted with tert-butyl methyl ether. The organic phase is washed three times with water, dried over Na₂SO₄, filtered and concentrated to dryness by evaporation. 200.63 g of crude product are obtained, which are purified by chromatography over silica gel using ethyl acetate/acetonitrile (9:1) as eluant to yield 145.47 g (60% of the theoretical yield) of a pure compound of the formula

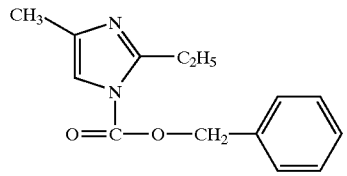

in the form of a colourless liquid.
Elemental Analysis:

| found | calculated |
|---|---|
| 68.84% C | 68.83% C |
| 6.49% H | 6.60% H |
| 11.38% N | 11.47% N. |

The ¹H NMR spectrum of the compound obtained corresponds to the formula given above.

EXAMPLE A25

5.32 g (50 mmol) of chloroformic acid vinyl ester are added dropwise in portions, with stirring, to a solution, maintained at below 2° C. using an ice-water bath, of 5.51 g (50 mmol) of 2-ethyl-4-methylimidazole and 5.56 g (55 mmol) of triethylamine in 70 ml of acetonitrile, the portions being such that the temperature of the reaction solution remains below 5° C. The ice-water bath is removed, and the reaction solution is allowed to warm up to room temperature and is then stirred at room temperature for a further hour. The precipitate is filtered off, and the filtrate is extracted with tert-butyl methyl ether. The organic phase is washed five times with water, dried over $Na_2SO_4$, filtered and concentrated to dryness by evaporation to yield 8.36 g (93% of the theoretical yield) of a pure compound of the formula

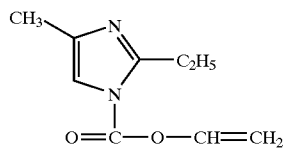

in the form of a colourdess liquid.

Elemental Analysis:

| found | calculated |
|---|---|
| 59.47% C | 59.99% C |
| 7.11% H | 6.71% H |
| 14.89% N | 15.55% N. |

The $^1$H NMR spectrum of the compound obtained corresponds to the formula given above.

EXAMPLE A26

10.78 g (50 mmol) of chloroformic acid 4-nitrobenzyl ester are added dropwise in portions, with stirring, to a solution, maintained at below 5° C. using an ice-water bath, of 5.51 g (50 mmol) of 2-ethyl-4-methylimidazole and 5.56 g (55 mmol) of triethylamine in 70 ml of acetonitrile, the portions being such that the temperature of the reaction solution remains below 5° C. The ice-water bath is removed, and the reaction solution is allowed to warm up to room temperature and is stirred at room temperature overnight. The precipitate formed is filtered off, and the filtrate is extracted with tert-butyl methyl ether. The organic phase is washed five times with water, dried over $Na_2SO_4$, filtered and concentrated to dryness by evaporation. A slightly yellow solid substance is obtained, which is recrystallised from tert-butyl methyl ether to yield 9.32 g (64% of the theoretical yield) of a pure compound of the formula

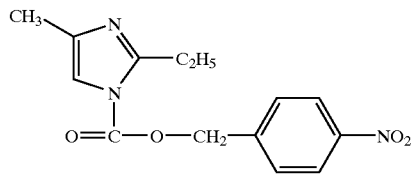

in the form of colourless crystals that melt at 106.1° C.

Elemental Analysis:

| found | calculated |
|---|---|
| 58.11% C | 58.13% C |
| 5.22% H | 5.23% H |
| 14.59% N | 14.53% N. |

The $^1$H NMR spectrum of the compound obtained corresponds to the formula given above.

EXAMPLE A27

0.50 g (1.8 mmol) of chloroformic acid 6-nitroveratryl ester is added dropwise in portions, with stirring, to a solution, maintained at below 2° C. using an ice-water bath, of 0.2 g (1.8 mmol) of 2-ethylimidazole and 0.20 g (2 mmol) of triethylamine in a solvent mixture of 25 ml of acetonitrile and 30 ml of tert-butyl ethyl ether, the portions being such that the temperature of the reaction solution remains below 5° C. The ice-water bath is removed, and the reaction solution is allowed to warm up to room temperature and is then stirred at room temperature for a further 2 hours. The precipitate is filtered off, and the filtrate is extracted with tert-butyl methyl ether. The organic phase is washed three times with water, dried over $Na_2SO_4$, filtered and concentrated to dryness by evaporation. The crude product is triturated in hexane and filtered. The filtrate is concentrated to dryness by evaporation and dried in a vacuum oven at 40° C. 0.39 g (62% of the theoretical yield) of a pure compound of the formula

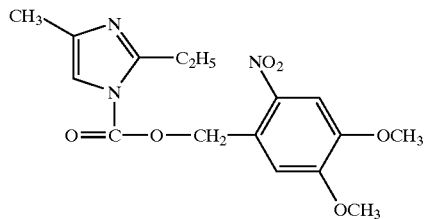

is obtained in the form of a solid beige substance having a melting point of 129.4° C.

Elemental Analysis:

| found | calculated |
|---|---|
| 54.84% C | 55.01% C |
| 5.48% H | 5.44% H |
| 12.05% N | 12.03% N. |

The $^1$H NMR spectrum of the compound obtained corresponds to the formula given above.

EXAMPLE A28

The process set out in Example 2 is repeated using 2-ethylmethylimidazole instead of imidazole to yield a compound of the formula

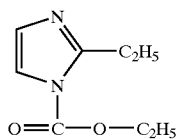

Yield: 69% of the theoretical yield.
Elemental Analysis:

| found | calculated |
|---|---|
| 56.94% C | 57.13% C |
| 7.24% H | 7.19% H |
| 16.65% N | 16.66% N. |

EXAMPLE A29

5.32 g (50 mmol) of chloroformic acid vinyl ester are added dropwise in portions, with stirring, to a solution, maintained at below 5° C. using an ice-water bath, of 9.61 g (0.1 mol) of 2-ethylimidazole and 11.13 g (0.11 mol) of triethylamine in 150 ml of acetonitrile, the portions being such that the temperature of the reaction solution remains below 5° C. The ice-water bath is removed, and the reaction solution is allowed to warm up to room temperature and is then stirred at room temperature for a further 3 hours. The precipitate is filtered off, and the filtrate is extracted with 300 ml of tert-butyl methyl ether and 500 ml of water. The organic phase is washed three times with water, dried over $Na_2SO_4$, filtered and concentrated to dryness by evaporation. 13.03 g of crude product are obtained, which are purified by chromatography over silica gel using Ethylacetate/acetonitrile (9:1) as eluant, the fractions 12–32 being combined and concentrated to dryness. 9.73 g (42% of the theoretical yield) of a pure compound of the formula

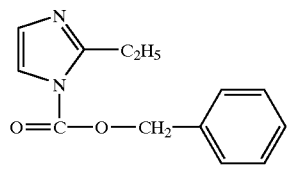

are obtained in the form of a colourless liquid.
Elemental Analysis:

| found | calculated |
|---|---|
| 67.79% C | 67.81% C |
| 6.27% H | 6.13% H |
| 11.87% N | 12.17% N. |

The $^1$H NMR spectrum of the compound obtained corresponds to the formula given above.

EXAMPLE A30

0.57 g (5.1 mmol) of chloroformic acid ethyl ester is added dropwise in portions, with stirring, to a solution, maintained at below 3° C. using an ice-water bath, of 1.15 g (5.1 mmol) of 4,5-diphenylimidazole and 0.57 g (5.6 mmol) of triethylamine in 60 ml of acetonitrile, the portions being such that the temperature of the reaction solution remains below 5° C. The ice-water bath is removed, and the reaction solution is allowed to warm up to room temperature and is then stirred further overnight. The precipitates is filtered off, and the filtrate is concentrated to dryness by evaporation. The residue is taken up in 50 ml of dichloroethane, washed three times with water, dried over $Na_2SO_4$, filtered and concentrated to dryness by evaporation. 0.94 g of a crude product is obtained, which is triturated in hexane. Filtration and evaporation of the organic solvent yield 0.56 g (37% of the theoretical yield) of a pure compound of the formula

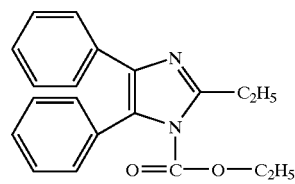

in the form of a white powder having a melting point of 97.0° C.
Elemental Analysis:

| found | calculated |
|---|---|
| 73.87% C | 73.97% C |
| 5.70% H | 5.48% H |
| 9.31% N | 9.59% N. |

The $^1$H NMR spectrum of the compound obtained corresponds to the formula given above.

EXAMPLE A31

The process set out in Example 2 is repeated using 2-isopropylimidazole instead of imidazole to yield a compound of the formula

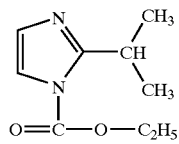

Yield: 21% of the theoretical yield.
Elemental Analysis:

| found | calculated |
|---|---|
| 66.59% C | 66.65% C |
| 5.67% H | 5.59% H |
| 12.95% N | 12.96% N. |

EXAMPLE A32

A solution of 200 g (0.92 mol) of di-tert-butyl dicarbonate in 200 ml of tetrahydrofuran is added dropwise, with stirring, to a solution, maintained at below 20° C. using an ice-water bath, of 100 g (0.92 mol) of 2-isopropylimidazole and 11.2 g (0.092 mol) of 4-dimethyl-aminopyridine in 600 ml of tetrahydrofuran. The reaction mixture is then stirred overnight at room temperature. The solvent is then evaporated off, and the residue is taken up in 100 ml of hexane and washed five times with 200 ml of water. The organic phase is dried over Na₂SO₄, filtered and concentrated to dryness by evaporation. 147.2 g (77% of the theoretical yield) of a pure compound of the formula

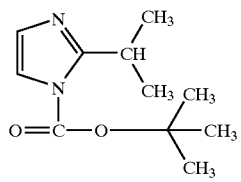

are obtained in the form of a yellow liquid.
Elemental Analysis:

| found | calculated |
|---|---|
| 62.83% C | 63.16% C |
| 8.83% H | 8.13% H |
| 13.31% N | 13.40% N. |

The ¹H NMR spectrum of the compound obtained corresponds to the formula given above.

EXAMPLE A33

A solution of 34.4 g (0.22 mol) of chloroformic acid phenyl ester in 460 ml of acetonitrile is added dropwise, with stirring, to a solution, maintained at below 20° C. using an ice-water bath, of 24.2 g (0.92 mol) of 2-isopropylimidazole and 26.6 g (0.23 mol) of triethylamine in 460 ml of acetonitrile. The reaction mixture is then stirred overnight at room temperature. The solvent is then evaporated off, and the residue is dissolved in 200 ml of tert-butyl ethyl ether and washed five times with 100 ml of water. The organic phase is dried over Na₂SO₄, filtered and concentrated to dryness by evaporation. 42.8 g (84% of the theoretical yield) of a pure compound of the formula

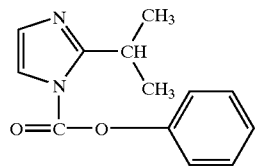

are obtained in the form of a slightly yellow solid substance having a melting point of 68.6° C.
Elemental Analysis:

| found | calculated |
|---|---|
| 67.77% C | 67.24% C |
| 6.53% H | 6.90% H |
| 12.11% N | 12.07% N. |

The ¹H NMR spectrum of the compound obtained corresponds to the formula given above.

EXAMPLE A34

2.91 g (0.011 mol) of chloroformic acid 6-nitroveratryl ester are added in portions, with stirring, to a solution, maintained at below 2° C. using an ice-water bath, of 1.15 g (0.011 mol) of 2-isopropylimidazole and 1.17 g (0.012 mol) of triethylamine in 100 ml of acetonitrile, the portions being such that the temperature of the reaction mixture is kept below 5° C. The reaction mixture is then allowed to warm up to room temperature and is stirred overnight at room temperature. After filtration of the yellow suspension, the solvent is evaporated off from the filtrate. The resulting residue is taken up in 100 ml of dichloromethane and washed three times with water. The organic phase is dried over Na₂SO₄, filtered and concentrated to dryness by evaporation. 3.08 g (84% of the theoretical yield) of a pure compound of the formula

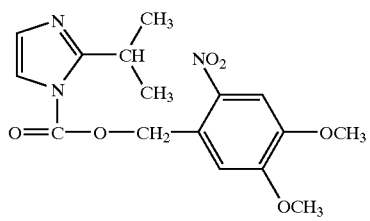

are obtained in the form of a slightly yellow powder having a melting point of 137.9° C.

Elemental Analysis:

| found | calculated |
|---|---|
| 54.75% C | 55.17% C |
| 5.53% H | 5.17% H |
| 11.90% N | 12.07% N. |

The ¹H NMR spectrum of the compound obtained corresponds to the formula given above.

EXAMPLE A35

5.42 g (50 mmol) of chloroformic acid ethyl ester are added dropwise in portions, to a stirred solution of 7.55 g (25 mmol) of 2-heptadecylimidazole and 2.78 g (27 mmol) of triethylamine in 100 ml of cyclohexanol, the portions being such that the temperature of the reaction mixture remains below 25° C. The reaction mixture is stirred overnight and then the yellowish precipitate is removed by filtration, and the cyclohexanol is evaporated off from the filtrate. The residue is dissolved in 400 ml of tert-butyl ethyl ether and washed four times with water. The organic phase is dried over Na₂SO₄, filtered and concentrated to dryness by evaporation. 7.94 g (42% of the theoretical yield) of a pure compound of the formula

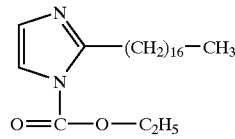

are obtained in the form of a dark-yellow solid substance having a melting point of 38.6° C.

Elemental Analysis:

| found | calculated |
|---|---|
| 72.71% C | 72.97% C |
| 11.20% H | 11.18% H |
| 7.24% N | 7.40% N. |

The $^1$H NMR spectrum of the compound obtained corresponds to the formula given above.

II. Measurement of the Gelling Time, at Different Temperatures, of Epoxy Resin Mixtures Comprising an Imidazole Compound of Formula I or II A mixture is prepared from 1 g of an epoxy resin comprising diglycidyl ether of bisphenol A and diglycidyl ether of bisphenol F, and having an epoxy value of 5.65 equivalents/kg, and $5.65 \cdot 10^{-4}$ mol of an imidazole compound of formula I or II according to Examples A1 to A35, and the gelling time of that mixture is determined at different temperatures by applying the curable epoxy resin mixture to a hot plate of the given temperature, and the time taken for the mixture to gel is measured. The following Table gives the times in hours (h), minutes (') and seconds (").

| Imidazole compound according to Example | Amount of imidazole comp. per g epoxy comp. | Gelling time of the epoxy resin mixture | | |
|---|---|---|---|---|
| | | at 100° | 130° | 150° C. |
| imidazole | 38.0 mg | 7'10" | 1'15" | 35" |
| A1 | 71.2 mg | 13'43" | 3'01" | 1'10" |
| A2 | 79.1 mg | 16'30" | 3'45" | 1'25" |
| A3 | 94.9 mg | 29'20" | 6'40" | 2'20" |
| A4 | 94.9 mg | 18'37" | 6'42" | 2'05" |
| A5 | 126.7 mg | 23'40" | 5'23" | 2'28" |
| A6 | 198.1 mg | 21'08" | 5'29" | 2'33" |
| A7 | 93.8 mg | 21'10" | 5'10" | 1'57" |
| A8 | 101.7 mg | 19'12" | 3'43" | 1'15" |
| A9 | 140.0 mg | 37'40" | 7'23" | 2'37" |
| A10 | 173.6 mg | 48'00" | 8'34" | 3'00" |
| A11 | 122.0 mg | 1 h 02' | 21'53" | 5'38" |
| A12 | 138.0 mg | 1 h 02' | 15'54" | 8'55" |
| A13 | 136.9 mg | 1 h 04' | 19'34" | 7'02" |
| A14 | | | not measured | |
| A15 | 132.2 mg | 1 h 10' | 17'04" | 8'52" |
| A16 | | | not measured | |
| A17 | 182.6 mg | 56'00" | 14'00" | 4'52" |
| A18 | 217.7 mg | 1 h 11' | 21'56" | 8'17" |
| A19 | 122.0 mg | 27'30" | 6'44" | 3'00" |
| A20 | 132.2 mg | 27'00" | 4'26" | 1'58" |
| A21 | 130.1 mg | 35'15" | 8'55" | 3'05" |
| A22 | 102.8 mg | 46'30" | 9'40" | 5'00" |
| A23 | 130.0 mg | 25'15" | 5'30" | 2'00" |
| A24 | 137.9 mg | 40'00" | 9'50" | 3'40" |
| A25 | 101.8 mg | 58'00" | 14'20" | 4'25" |
| A26 | 163.4 mg | 39'50" | 6'30" | 2'57" |
| A27 | 197.4 mg | 45'40" | 10'30" | 4'23" |
| A28 | 95.0 mg | 41'00" | 9'46" | 3'30" |
| A29 | 130.0 mg | 27'25" | 6'20" | 2'57" |
| A30 | 165.1 mg | 1 h 10' | 23'10" | 11'00" |
| A31 | 103.0 mg | 1 h 55' | 32'48" | 13'23" |
| A32 | 118.2 mg | 4 h 50' | 51'32" | 12'41" |
| A33 | 131.2 mg | 1 h 32' | 17'45" | 7'58" |
| A34 | 196.8 mg | 1 h 50' | 20'30" | 8'22" |
| A35 | 213.9 mg | 41'28" | 8'36" | 4'05". |

III. Measurement of the Viscosity of Epoxy Resin Mixtures Comprising an Imidazole Compound of Formula I or II Before and After Heating at 50° C. for Several Hours A mixture is prepared from an epoxy resin comprising diglycidyl ether of bisphenol A and diglycidyl ether of bisphenol F in a ratio of 15:37 parts by weight, and having an epoxy value of 5.65 equivalents/kg, and an imidazole compound of formula I or II according to Examples A11 to A35, using $5.65 \cdot 10^{-4}$ mol of an imidazole compound of formula I or II per gram of the epoxy resin. The viscosity of the epoxy resin mixtures is determined at 40° C., using an Epprecht viscometer, before heating and after heating at 50° C. for 8 and 24 hours.

| Imidazole compound according to Example | Viscosity of the epoxy resin mixture in mPa · s | | |
|---|---|---|---|
| | before heating | after heating at 50° C. for | |
| | | 8 h | 24 h |
| imidazole | 300 | polymerised | |
| A11 | 1180 | 1220 | |
| A12 | 960 | 1840 | |
| A13 | 640 | 1760 | |
| A14 | 1020 | 880 | |
| A15 | 510 | 8160 | |
| A16 | 1040 | 1440 | |
| A17 | 1720 | 9280 | |
| A18 | 2480 | 7680 | |
| A19 | 540 | 1100 | |
| A20 | 1100 | 1440 | |
| A21 | 580 | 6400 | |
| A22 | 430 | 9280 | |
| A23 | 760 | 12800 | |
| A24 | 540 | 2680 | |
| A25 | 500 | 3680 | |
| A26 | 1080 | 4320 | |
| A27 | 1280 | 2640 | |
| A30 | 300 | 940 | |
| A31 | 430 | 320 | |
| A32 | 410 | 240 | 900 |
| A33 | 720 | 4160 | polymerised |
| A34 | 1600 | 900 | 33920 |
| A35 | 400 | 560 | 740. |

IV. Manufacture of a Moulded Material 100 g of a diglycidyl ether of bisphenol A having an epoxy value of 5.54 equivalents/kg are mixed, at room temperature, with 14.5 g of the imidazole compound according to Example A20. That curable epoxy resin mixture has a gelling time of 6'15" at 130° C., a gelling time of 3'40" at 140° C. and a gelling time of 2'30" at 150° C. After curing for 15 minutes at 120° C., the moulded materials made from the curable epoxy resin mixture have a $T_g$ value of 103.4° C.

V. Manufacture of a Surface-coating 300 g of diglycidyl ether of bisphenol A having an epoxy value of 1.23–1.37 equivalents/kg, 15.0 g of a diglycidyl ether of bisphenol A having an epoxy value of 1.15–1.35 equivalents/kg, containing 10% by weight of the flow agent® Acrylon, 0.6 g of benzoin, 135.0 g of TiO$_2$ and 6.3 g of the imidazole compound according to Example A20 are mixed in an extruder. Sheet iron is electrostatically coated with the resulting powder which is stoved for 20 minutes at 120° C. Film thickness: 58 µm. The surface-coating has the following properties:

| | |
|---|---|
| Impact (reverse side)= | 160 cm/kg |
| Cupping index according to Erichsen= | 9.7 mm |
| Acetone test*= | film surface unchanged (best score) |
| Flow**= | score 8 |
| Gloss 60° C. (%)= | 106. |

*A cotton swab impregnated with acetone is placed on the coated surface for 1 minute. It is then tested whether the coating surface can be scratched with a finger nail.
**visual evaluation: score 4= best result, score 16= worst result.

What is claimed is:

1. A curable mixture comprising
a) an epoxy resin having more than one 1,2-epoxy group per molecule,
(b) as curing accelerator, an imidazole compound of formula I

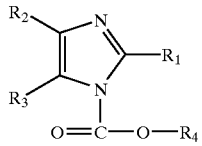

(I)

wherein R1, R2 and R3 are each independently of the others a hydrogen atom, a halogen atom, alkyl having from 1 to 20 carbon atoms, alkoxy having from 1 to 20 carbon atoms, unsubstituted or halo-, nitro-, C1–C4alkyl- or C1–C4alkoxy-substituted aralkyl having from 7 to 20 carbon atoms, or unsubstituted or halo-, nitro-, C1–C4alkyl- or C1–C4alkoxy-substituted aryl having from 6 to 20 carbon atoms, and R4 is alkyl having from 1 to 20 carbon atoms, alkenyl having from 2 to 20 carbon atoms, alkynyl having from 2 to 20 carbon atoms, unsubstituted or halo-, C1–C4alkyl- or C1–C4alkoxy-substituted aralkyl having from 7 to 20 carbon atoms or unsubstituted or halo-, C1–C4alkyl- or C1–C4alkoxy-substituted aryl having from 6 to 20 carbon atoms; and c) a curing agent for epoxy resins.

2. A mixture according to claim 1, comprising as component (c) dicyandiamide or a polycarboxylic acid anhydride.

3. A moulded material, coating or bonded material manufactured by curing from a curable mixture according to claim 1.

* * * * *

UNITED STATES PATENT AND TRADEMARK OFFICE
CERTIFICATE OF CORRECTION

PATENT NO. : 6,455,662 B2
DATED : September 24, 2002
INVENTOR(S) : Veronique Hall-Goulle It is certified that error appears in the above-identified patent and that said Letters Patent is hereby corrected as shown below:

Title page,
Item [75], the address of the inventor should read -- Reinach (CH) --;
Item [57], ABSTRACT,
Last line, "dicyadiamide" should read -- dicyandiamide --;

Column 1,
Line 59, "carded out" should read -- carried out --;

Column 6,
Line 17, "The compound of formula 11" should read -- The compound of formula II --;

Column 18,
Line 50, "mol) of, triethylamine" should read -- mol) of triethylamine --.

Signed and Sealed this

Second Day of November, 2004

JON W. DUDAS
*Director of the United States Patent and Trademark Office*